Figure 1:
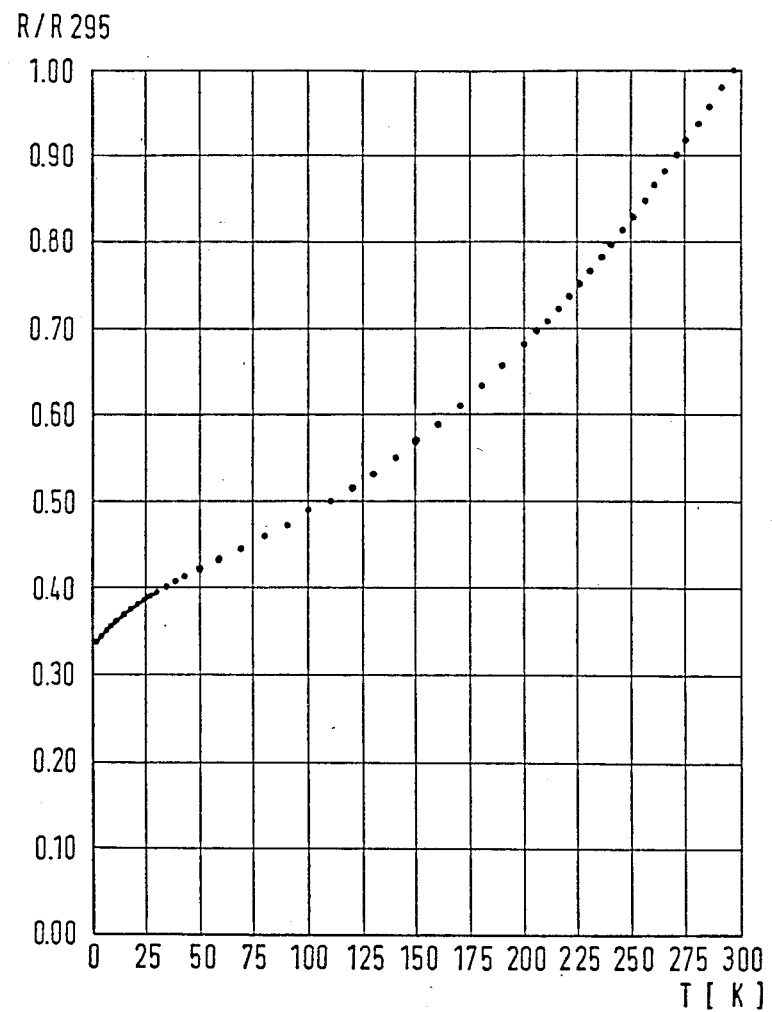

United States Patent [19]

Hilti et al.

[11] Patent Number: 4,801,701
[45] Date of Patent: Jan. 31, 1989

[54] DIFLUORINATED (5,6,11,12-TETRASELENOTETRACENE)2 HALIDES, THE PREPARATION THEREOF AND THE USE THEREOF

[75] Inventors: Bruno Hilti, Basel; Carl W. Mayer, Riehen, both of Switzerland

[73] Assignee: Ciba-Geigy Corporation, Ardsley, N.Y.

[21] Appl. No.: 917,112

[22] Filed: Oct. 8, 1986

[30] Foreign Application Priority Data

Oct. 18, 1985 [CH] Switzerland .......................... 4570/85

[51] Int. Cl.⁴ .......................................... C07D 517/06
[52] U.S. Cl. ....................................................... 540/1
[58] Field of Search ............................................ 540/1

[56] References Cited

U.S. PATENT DOCUMENTS

| | | | |
|---|---|---|---|
| 4,036,648 | 7/1977 | Engler et al. | 540/1 |
| 4,384,025 | 5/1983 | Hilti et al. | 540/1 |
| 4,522,754 | 6/1985 | Hilti et al. | 540/1 |
| 4,601,853 | 7/1986 | Hilti et al. | 540/1 |

FOREIGN PATENT DOCUMENTS 23988   2/1981   European Pat. Off. .............. 540/1

OTHER PUBLICATIONS

B. Hilti et al, Helv. Chim Acta, 61, 1462 (1978).

*Primary Examiner*—Robert Gerstl
*Attorney, Agent, or Firm*—Harry Falber; Luther A. R. Hall

[57] ABSTRACT

The invention relates to complexes of formula I

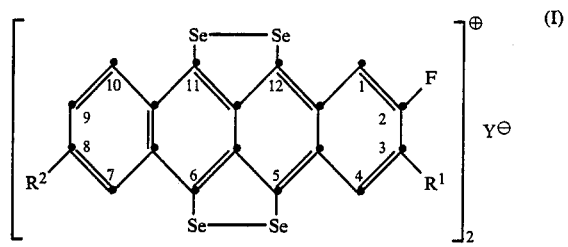

wherein $R^1$ is fluorine and $R^2$ is hydrogen, or $R^2$ is fluorine and $R^1$ is hydrogen, and Y is bromine, or Y is also chlorine when $R^1$ is hydrogen. These complexes are organic compounds which exhibit high electrical conductivity.

2 Claims, 1 Drawing Sheet

DIFLUORINATED (5,6,11,12-TETRASELENOTETRACENE)2 HALIDES, THE PREPARATION THEREOF AND THE USE THEREOF

The present invention relates to difluorinated (5,6,11,12-tetraselenotetracene)2 halides, to the preparation thereof and to the use thereof as electrical conductors or as components in electronic systems.

Metallically conductive tetracene complexes, e.g. (5,6,11,12-tetraselenotetracene)2 iodide, bromide or chloride, are known from the literature [q.v. e.g. B. Hilti et al, Helvetica Chimica Acta, Vol. 61, Fasc. 4, pp. 1462–1469 (1978)]. These complexes exhibit a relatively sharp transition from the metallic to the non-conductive state in the temperature range from about 30 to 5 K., i.e. the metallic phase is not stable down to temperatures at which, for example, supraconductivity can be expected.

(2-Fluoro-5,6,11,12-tetraselenotetracene)2 bromide is described in published European patent application No. 0 109 360. This complex exhibits metal conductivity down to low temperatures. However, it is not evident why the fluorine substitution brings about a stabilisation of the metallic phase down to low temperatures. Moreover, it is not possible to predict whether a further substitution would produce complexes exhibiting metallic conductivity and, if so, whether they would have a similar temperature dependence with respect to the metallic conductivity.

The present invention relates to a complex of formula I

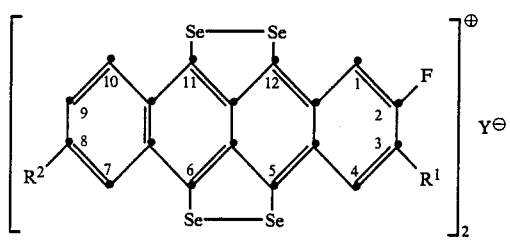

wherein $R^1$ is fluorine and $R^2$ is hydrogen, or $R^2$ is fluorine and $R^1$ is hydrogen, and Y is bromine, or Y is also chlorine when $R^1$ is hydrogen.

Surprisingly, the complexes of the present invention are distinguished by a metallic phase which is stable down to at least 2 K., i.e. in the temperature range from room temperature down to at least 2 K. the electrical conductivity increases. Moreover, down to about 50 K. the conductivity of the complexes increases monotonously and below this temperature in the case of the 2,3-substituted bromide the increase in conductivity accelerates. At room temperature the conductivity is about 2000 $ohm^{-1}cm^{-1}$ and at 2 K. it is about 6000 $ohm^{-1}cm^{-1}$, measured along the preferred direction of growth (needle axis). The complexes of this invention have the orthogonal space group $P2_12_12$.

The complexes of this invention can be employed as electrical conductors e.g. in the form of microcrystalline powders, as an amorphous layer, as a layer of microcrystals, as an amorphous powder or in the form of monocrystals.

The present invention further relates to a process for the preparation of complexes of formula I, which process comprises oxidising a compound of formula II

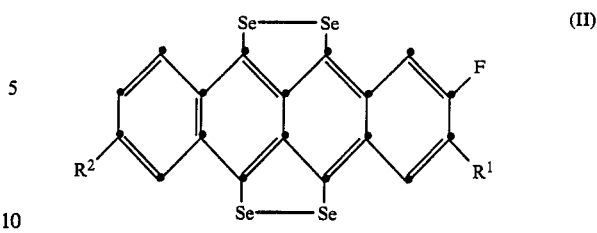

wherein $R^1$ and $R^2$ are as defined for formula I, with chlorine or bromine.

The complexes of formula I can be prepared by various oxidation methods, for example by (direct) oxidation of a difluoro-5,6,11,12-tetraselenotetracene with chlorine or bromine or with an oxidising chlorine salt which releases chloride or bromide, e.g. copper(II) chloride and $FeCl_3$, in the presence of an inert organic solvent. Examples of suitable inert organic solvents are halogenated aliphatic hydrocarbons such as methylene chloride and 1,1,2-trichloroethane; polar substituted, in particular halogenated, aromatic hydrocarbons such as chlorobenzene, o-dichlorobenzene, 1,2,3-trichlorobenzene, 1,2,4-trichlorobenzene and chlorinated napthalenes; other polar solvents such as benzonitrile and alkylnitriles containing 2 to 5 carbon atoms, e.g. acetonitrile, propionitrile and butyronitrile; nitrobenzene; N,N-dialkylamides of aliphatic monocarboxylic acids containing 1 to 4 carbon atoms in the acid moiety, e.g. N,N-dimethylformamide and N,N-dimethylacetamide; N,N,N',N'-tetramethylurea; dialkyl sulfoxides such as dimethyl sulfoxide and diethyl sulfoxide; and cyclic ethers such as tetrahydropyran, tetrahydrofuran and dioxane. Mixtures of the solvents mentioned can also be used. The reaction temperatures in these oxidation reactions are in general in the range from 20° to 120° C.

The complexes of formula I can also be prepared by diffusion of chlorine or bromine from the gas phase or from a carrier solution into a solution of a difluoro-5,6,11,12-tetraselenotetracene, suitable solvents being those of the above-mentioned type.

Furthermore, the complexes of formula I can be prepared from the gas phase, i.e. by cosublimation of a difluoro-5,6,11,12-tetraselenotracene and chlorine or bromine by a process analogous to that described in German patent specification No. 26 41 742. In this process, a difluoro-5,6,11,12-tetraselenotetracene and chloride or bromine are advantageously allowed to react with one another in an inert gas atmosphere, preferably in an open system. However, the reaction in the gas phase can also be carried out in a closed system in an inert gas atmosphere. The reaction in the gas phase can be carried out, for example, by bringing chlorine gas or bromine gas into contact with a difluoro-5,6,11,12-tetraselenotetracene by means of an inert carrier gas in the gas phase at about 260° C. In this procedure, the crystals grow in any desired form, for example in the form of rods or tubes, on the reactor walls and/or any substrate which may be located in the reactor, e.g. aluminium oxide or, preferably, quartz. The carrier gases used in this preparatory method are advantageously high-purity inert gases such as argon, nitrogen, helium and xenon. The reaction temperatures in the gas phase reaction are advantageously in the range from 180° to 300° C. The crystals obtained by a gas phase reaction can readily be removed from the reaction chamber or from the substrate. A suitable experimental arrangement for this preparatory method is described in the above-mentioned German patent specification No. 26 41 742.

Preferably, however, the complexes of this invention are prepared be electrochemical oxidation of a difluoro-5,6,11,12-tetraselenotetracene in the presence of an inert organic solvent and a chloride-containing or bromide-containing conductive salt. Suitable inert organic solvents are those of the above-mentioned type. Preferred solvents are cyclic ethers and N,N-dialkylamides of aliphatic monocarboxylic acids or mixtures thereof, e.g. tetrahydrofuran and N,N-dimethylformamide or mixtures thereof. Examples of suitable conductive salts are salts of the formula

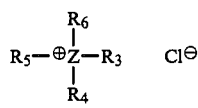

wherein Z is N, P or As and each of $R_3$ to $R_6$ independently is $C_1$-$C_{18}$alkyl, benzyl, phenyl or naphthyl, and corresponding bromides. Alkyl groups $R_3$ to $R_6$ can be straight chain or branched and preferably contain 1 to 12 carbon atoms. Examples of such alkyl groups are: methyl, ethyl, n-propyl, isopropyl, n-butyl, sec-butyl, tert-butyl, 1,1,3,3-tetramethylbutyl, n-pentyl, 2-pentyl, n-hexyl, n-heptyl, n-octyl, n-decyl, n-dodecyl, n-tetradecyl, n-hexadecyl and n-octadecyl. It is preferred to use those conductive salts wherein Z is N or P, $R_3$ is benzyl or phenyl and each of $R_4$ to $R_6$ is straight chain alkyl containing 1 to 12 carbon atoms or phenyl, or each of $R_3$ to $R_6$ is straight chain alkyl containing 1 to 12 carbon atoms. It is particularly preferred to use those conductive salts wherein Z is N and each of $R_3$ to $R_6$ is straight chain alkyl containing 1 to 12 carbon atoms, in particular n-hexyl.

Depending on the temperature of the electrolysis cell and the solvent employed, it is advantageous to use between 0.01 and 30 g of conductive salt per liter. Devices which are known per se can be used as the electrolysis cells, for example those in which the anode compartment is separated from the cathode compartment by a Teflon screen glass frits or capillaries. The dimensions of the electrolysis cells can vary depending on the amount of reaction components used and have virtually no adverse effect on the quality of the complex of formula I obtained. Cell volumes of, for example, 15–100 ml are particularly suitable for the preparation of about 5–50 mg of complex of formula I.

The reaction temperatures (temperatures of the electrolysis cells) are advantageously in the range from 0° and 120° C., depending on the nature of the solvent used. The current strength varies in general between 0.005 $\mu$A and 5 $\mu$A. The diameter of the anodes and cathodes is advantageously between 0.1 and 5 mm.

In the above reactions, at least stoichiometric amounts of a difluoro-5,6,11,12-tetraselenotetracene and chlorine or bromine or a chloride or bromide salt are employed. However, it is generally advisable to start with an excess of chlorine or bromine or chloride or bromide salt, so that there is a onefold to thousandfold molar excess of chlorine or bromine or chloride or bromide salt in the reaction phase at any time.

The 2,3-difluoro-substituted tetracenes of formula II can be obtained in accordance with the following reaction schemes:

The known 4,5-difluorophthalic anhydride is reacted with the likewise known 1,4-hydronaphthoquinone, in the presence of boron trioxide and in the melt, to give a compound of formula IV

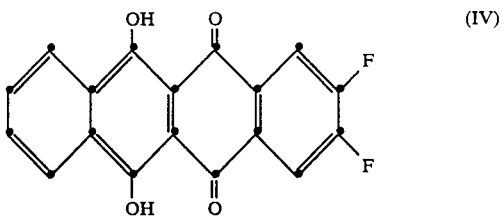

(q.v. CH. Weismann et al, J. Chem. Soc. 1939, pp. 398–401). The compound of formula IV is chlorinated with PCl$_5$, in the temperature range from about 100° to 200° C., to give the compound of the formula V

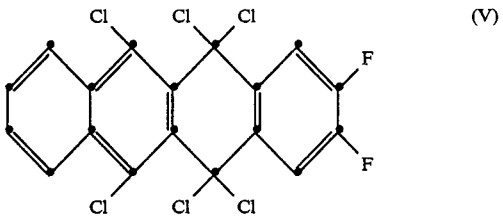

[q.v. Baladis et al, Zh. Org. Chim. 15(2), pp. 298–401 (1979)] which is converted into the tetrachlorine compound of formula VI

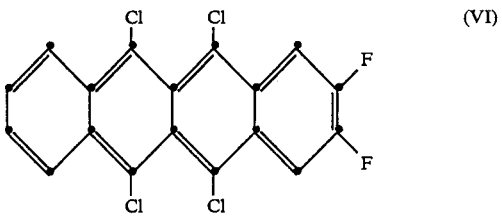

by treatment with SnCl$_2$ in an acid reaction medium (acetic acid) in the temperature range from about 50° to 150° C. The compound of formula VI is reacted with Na$_2$Se$_2$, in a polar aprotic solvent, e.g. dimethylformamide, and in the temperature range from about 40° to 100° C., to give the compound of formula VII

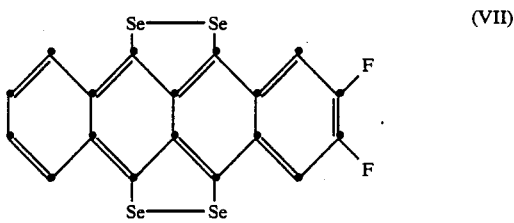

The 2,8-difluorinated tetracenes of formula II can be obtained in accordance with the following reaction schemes:

The double Stobbe condensation of p-fluorobenzaldehyde with succinic acid diesters, e.g. diethyl esters, and subsequent hydrolytic working up yields fulgenic acid of formula VIII [q.v. K. Freudenberg et al, Annalen der Chemie 602, pp. 184–191, (1957)]

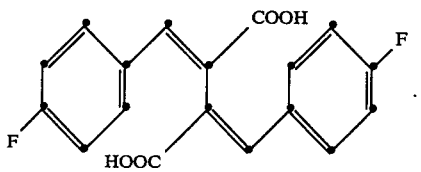

(VIII)

This dicarboxylic acid can be first etherified, e.g. with ethyl alcohol, and then treated with concentrated sulfuric acid. Alternatively, said dicarboxylic acid, dissolved in e.g. 1,2,4-trichlorobenzene, can be treated direct with a Lewis acid, e.g. AlCl$_3$. In both cases the compound of formula IX

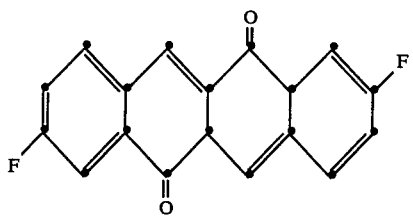

(IX)

is obtained. Following the procedure described above, the compound of formula IX is reacted with PCl$_5$ and the resultant compound is treated with SnCl$_2$ to give 2,8-difluoro-5,6,11,12-tetrachlorotetracene, which is reacted with Na$_2$Se$_2$ to yield the compound of formula X

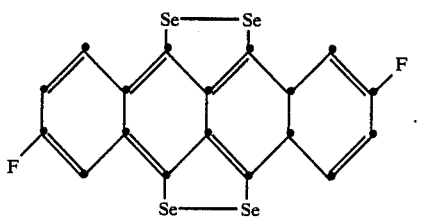

(X)

The present invention further relates to the novel intermediates of formulae IV to X, in particular to those of formula III

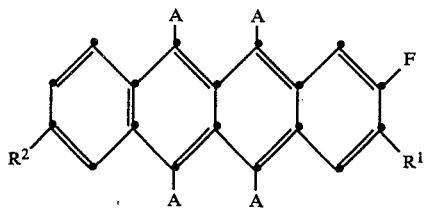

(III)

wherein R$^1$ and R$^2$ are as defined above and A is Cl, or each pair of substituents A in the peri-position is —Se—Se—.

On account of the metallically electrical conductivity and the pronounced electrical and optical anisotropy, the complexes of the invention are suitable for use as organic electrical conductors, for example for conductive coatings on plastic fibres; and furthermore as polariser material or as additives to antistatic coatings and coverings, for example those based on plastic. The complexes of formula I can also be employed in highly conductive printing materials or processes which are sensitive towards electron beams or are photosensitive, such as those described e.g. in published European patent application No. 0 023 988 and U.S. patent specification No. 4,036,648. Owing to their redox properties and their various intensive colours (green, cyan, blue and yellow, depending on the oxidation stage), the complexes of formula I can also be used advantageously in display and information systems such as colour display screens, and in electronic components. The highly conductive complexes of formula I are particularly suitable for such purposes since they can be subjected to further oxidation and reduction in electrical arrangements, e.g. electrochromic circuits. However, on the basis of their metallic phase which is stable at least down to about 2 K., the complexes of the invention are particularly suitable for various applications in low-temperature technology, for example for use as an electrically conductive layer in condenser films or as active battery electrodes, e.g. as cathode material in solid electrolyte cells, which can thus also be used at a low temperature. The complexes can also be used for pressure- and/or temperature-dependent circuit elements or for circuit elements which depend on a magnetic field.

FIG. 1 shows the dependence of the specific electrical resistance on temperature for (2,3-difluoro-5,6,11,12-tetraselenotetracene)$_2$ bromide.

The invention is illustrated in more detail by the following Examples.

(A) Preparation of difluoro-5,6,11,12-tetraselenotetracenes (a) Preparation of 2,3-difluoro-5,6,11,12-tetraselenotetracene (1)

2,3-Difluoro-6,11-hydroxy-5,12-naphthacenequinone 8.64 g of 4,5-difluorophthalic anhydride are mixed with 9.21 g of 1,4-naphthohydroquinone and 6.14 g of B$_2$O$_3$. With stirring, the mixture is heated in a 250 ml three-necked round flask to a bath temperature of 200° C. At about 130° C. a dark melt forms. The melt is kept at 200° C. for 2 hours, during which time it solidifies. The solid melt is cooled to 130° C., and 150 ml of water are added. The batch is heated under reflux for 1 hour, and the resultant wine-red precipitate is isolated by filtration, washed with water and ethanol and then boiled out with hot ethanol. The precipitate is subsequently dried under a high vacuum at 50° C., affording 8.67 g of crude product, which is purified by sublimation at 210° C./0.0013 mbar. Yield: 6.68 g of rusty brown crystals.

(2)

2,3-Difluoro-5,6,6,11,12-hexachloro-5,11-dihydrotetracene 6.68 g of the product obtained according to Example a1 are mixed in a mortar with 25.5 g of phosphorus pentachloride. The mixture is charged into a preheated (bath temperature=200° C.) 250 ml three-necked round flask and kept under reflux at 120° C. until it turns distinctly yellow. The mixture is kept at a bath temperature of 200° C. for a further 1 hour and then cooled to room temperature. With ice-bath cooling, 132 ml of acetic acid are added dropwise. The mixture is then stirred until it has warmed to room temperature. The resultant yellow precipitate is isolated by filtration, washed with acetic acid and dried under a high vacuum at 50° C. Yield: 7.98 g (83% of theory) of product.

(3) 2,3-Difluoro-5,6,11,12-tetrachlorotetracene

A round-necked flask is charged with 1.63 g of the product obtained according to Example a2, 61 ml of acetic acid, 6.5 g of tin(II) chloride dihydrate and 6.7 ml of concentrated hydrochloric acid. The batch is heated for 1 hour under reflux and then cooled and the resultant reddish beige precipitate is isolated by filtration, washed with acetic acid and dried under a high vacuum at 50° C., affording 1.25 g of crude product, which is chromatographed through silica gel (eluant: CCl₄). Yield: 170 mg (12.3% of theory) of product. In order to prepare sufficient amounts, the procedure is repeated.

(4) 2,3-Difluoro-5,6,11,12-tetraselenotetracene

Under an atmosphere of argon, a 100 ml of sulfurating flask is charged with 396 mg of selenium, 117 mg of sodium and 22 ml of dimethylformamide. The batch is heated to a bath temperature of 110° C. and kept at this temperature for 1 hour and then cooled to 50° C. To the resultant red solution are added 436.7 g of product obtained according to Example a3 and a further 22 ml of dimethylformamide. The mixture turns green. Said mixture is stirred for a further 18 hours at a bath temperature of 55° C. The resultant precipitate is isolated by suction filtration, washed with dimethylformamide, chloroform, benzene and acetone and dried under a high vacuum, affording 0.6 g of crude product. 174 mg of the crude product are sublimed at 280° C./0.0013 mbar. Yield: 25.9 mg of 2,3-difluoro-5,6,11,12-tetraselenotetracene.

(b) Preparation of 2,8-difluoro-5,6,11,12-tetraselenotetracene

(1) Preparation of

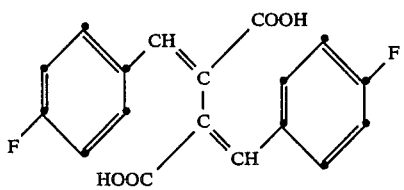

Under an atmosphere of argon, a 350 ml three-necked flask is charged with 22.4 g of sodium tert-butylate and 120 ml of toluene, and the batch is cooled to −15° C. With cooling, a mixture of 24.8 g of 4-fluorobenzaldehyde and 17.4 g of diethyl succinate is added drowise. When half of said mixture has been added, a further 120 ml of toluene are added. The remainder of the mixture of 4-fluorobenzaldehyde and diethyl succinate is then added dropwise over 80 minutes. The temperature is then allowed to rise to 2°–3° C. and the reaction mixture is stirred for 48 hours at this temperature. After the addition of 300 ml of ether, the reaction mixture is extracted with water and the ether phase is separated. The aqueous phase is extracted three times with ether and the other extracts are acidified with dilute hydrochloric acid and extracted three more times with ether. The ether phases are combined and extracted twice with water and the aqueous organic extracts are dried over Na₂SO₄ and filtered. The filtrate is then concentrated by evaporation, affording 33.2 g of crude product, which is dissolved in 100 ml of ether and 200 ml of benzene. The addition of 1 liter of hexane causes the product to precipitate. The product is isolated by suction filtration, washed with hexane and dried under a high vacuum, affording 13.8 g of pre-purified product, which is purified by subliming 8.0 g at 190°–195° C./0.0013 mbar. Yield: 4.9 g.

(2) Preparation of the diethyl ester of the product obtained according to Example b1

A 500 ml three-necked flask is charged with 2.0 g of the product obtained according to Example b1 and 200 ml of ethanol. The batch is cooled with an ice-bath and dry HCl gas is introduced until saturation point is reached. The mixture is allowed to warm to room temperature and is then stirred overnight. In the course of 5 hours, the temperature is increased to reflux temperature. HCl gas is introduced and the mixture is heated under reflux for 13 hours. The mixture is allowed to cool and is then concentrated by rotary evaporation, affording 1.9 g of product, which is purified through silica gel (eluant: a 4:1 mixture of hexane and ethyl acetate).
Yield: 1.75 g.

(3) Preparation of 2,8-difluoronaphthacene-6,12-quinone 2 g of the product obtained according to Example b2 and 200 ml of concentrated sulfuric acid are kept at 10° C. for 2 hours. The mixture is allowed to cool to room temperature and is then poured into ice-water and extracted with 2 liters of chloroform. The organic phase is separated through a phase filter, washed in succession with water, a 1:1 mixture of HCl and water, 10% NaHCO₃ and again with water and dried over Na₂SO₄. The solvent is evaporated off and the residue is purified by chromatography through silica gel (eluant: CHCl₃). Yield: 480 mg.

(4) Preparation of 2,8-difluoro-5,6,6,11,12-hexachlorodihydrotetracene 237 mg of the product obtained according to Example b3 and 3.5 g of PCl₅ are mixed. The mixture is heated to 200° C. and kept at this temperature for 40 minutes. After cooling, 35 ml of acetic acid are added, the mixture is stirred for 15 minutes and the precipitate is then isolated. Yield: 121 mg.

(5) Preparation of 2,8-difluoro-5,6,11,12-tetrachlorotetracene 121 mg of the product obtained according to Example b3, 12 ml of acetic acid, 1.2 g of SnCl₂.2H₂O and 1.2 ml of concentrated hydrochloric acid are mixed. The mixture is heated under reflux for 1 hour. After cooling, the mixture is diluted with 50 ml of water and the red precipitate is isolated by suction filtration, washed with water and dried under a high vacuum. Yield: 91 mg.

(6) Preparation of 2,8-difluoro-5,6,11,12-tetraselenotetracene 57.5 mg of selenium, 16.4 mg of sodium and 5 ml of dimethylformamide are mixed. The mixture is stirred for 1 hour at 120° C. under an atmosphere of argon and then cooled to 55° C. 54 mg of the product obtained according to Example b5 and 5 ml of dimethylformamide are added, and the mixture is stirred for 20 hours at this temperature. The mixture is then allowed to cool, and the precipitate is isolated by suction filtration and washed with dimethylformamide, chloroform, benzene and then with acetone. After drying, the precipitate is purified by sublimation at 275° C./0.0013 mbar. Yield: 14.7 mg.

EXAMPLE 1

10 mg of purified 2,3-F$_2$TSeT and 10 mg of purified 2,8-F$_2$TSeT are put into the anode compartment of separate 40 ml electrolyte cells. Under argon, 90 mg of tetrabutylammonium bromide are introduced as electrolyte into each cell. Nitrobenzene is employed as solvent. After 14 hours' heating at 70° C., a voltage of 0.1 volt is applied for 10 hours to each cell. Over the following 2 days, the voltage is increased in 3 stages to 0.5 volt, whereupon a current of 0.05 μA commences to flow in both cells. After 7 weeks, the crystals which have grown at the anodes (diameter 1 mm, Pt) are collected by washing with alcohol.

2 crystals (2 mm×5 μm×5 μm) of 2,3-F$_2$TSeTBr$_{0.5}$ are mounted onto each of four 15 μm thick gold wires using platinum paste (308 A Degussa). 2 crystals (2 mm×5 μm×5 μm) of 2,8F$_2$TSeTBr$_{0.5}$ are likewise mounted onto each of four 15 μm thick gold wires. The conductivity of all the crystals at room temperature, measured in the above four-probe arrangements, is 2000 ohm$^{-1}$cm$^{-1}$. All the crystals have a metallic phase down to the lowest limit of measurement of 2 K. In the case of 2,3-F$_2$TSeTBr$_{0.5}$ an accelerated decrease in specific resistance can be observed from 50 K. down to 2 K. (FIG. 1). Determination of the crystal structure by X-ray analysis shows that 2,3-F$_2$TSeTBr$_{0.5}$ and 2,8-F$_2$TSeTBr$_{0.5}$ both have the orthogonal space group P2$_1$2$_1$2. The cell constants for 2,3-F$_2$TSeTBr$_{0.5}$ are a: 17.766 Å, b: 17.766 Å and c: 5.133 Å. F$_2$TSeT stands for difluoro-5,6,11,12-tetraselenotetracene.

EXAMPLE 2

10 mg of purified 2,8-F$_2$TSeT are put into the anode compartment of a 40 ml electrolyte cell. Under argon, 90 mg of tetrahexylammonium chloride are introduced as electrolyte into the cell. Nitrobenzene is employed as solvent. After 14 hours' heating at 70° C., a voltage of 0.8 volt is applied to the cell. Over the following days, this voltage is increased in 3 stages to 1.2 volts, whereupon a current of 0.06 μA commences to flow in the cell. After 7 weeks, the crystals which have grown at the anode (diameter 1 mm; Pt) are collected by washing with alcohol.

2 crystals (2 mm×4 μm×4 μm) of 2,8-F$_2$TSeTCl$_{0.5}$ are examined in accordance with the procedure of Example 1. The conductivity at room temperature is 1500 ohm$^{-1}$cm$^{-1}$; the temperature dependence of the specific resistance is metallic down to the lowest limit of measurement of 2 K. X-Ray analysis of the structure of the crystals shows that they have the orthogonal space group P2$_1$2$_1$2 and the above-mentioned composition 2,8-F$_2$TSeTCl$_{0.5}$.

What is claimed is:

1. A complex formula I

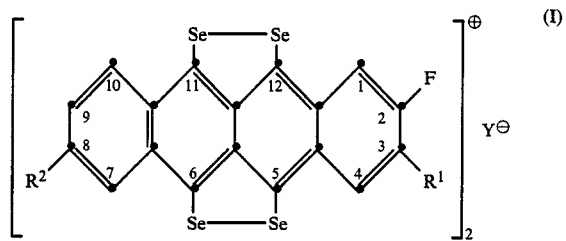

wherein R$^1$ is fluorine and R$^2$ is hydrogen, or R$^2$ is fluorine and R$^1$ is hydrogen, and Y is bromine, or Y is also chlorine when R$^1$ is hydrogen.

2. A compound of the formula

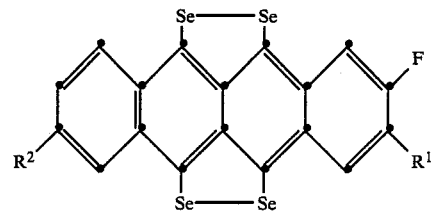

wherein R$^1$ is fluorine and R$^2$ is hydrogen, or R$^1$ is hydrogen and R$^2$ is fluorine.

* * * * *